United States Patent [19]

Someno et al.

[11] Patent Number: 4,525,465

[45] Date of Patent: Jun. 25, 1985

[54] WATER-INSOLUBLE BIOSPECIFIC ABSORBENT CONTAINING ARGININAL DERIVATIVE

[75] Inventors: Tetsuya Someno, Oomiya; Kazuo Kato, Urawa; Tetsushi Saino, Yono; Shinichi Ishii, Sapporo; Tomio Takeuchi; Hamao Umezawa, both of Tokyo, all of Japan

[73] Assignee: Nippon Kayaku Kabushiki Kaisha, Tokyo, Japan

[21] Appl. No.: 540,125

[22] Filed: Oct. 7, 1983

[51] Int. Cl.[3] ........................ B01J 20/26; C12N 9/72; A61K 37/54; C07C 103/52

[52] U.S. Cl. ........................................ 502/7; 210/656; 260/112.5 R; 435/179; 435/181; 435/215; 502/403; 502/404

[58] Field of Search ............... 502/159, 404, 403, 402, 502/401.7; 435/178–181, 215, 174, 176; 210/632, 635, 656, 927

[56] References Cited

U.S. PATENT DOCUMENTS

| | | | |
|---|---|---|---|
| 4,259,447 | 3/1981 | Hafeli | 435/215 |
| 4,334,972 | 6/1982 | Soderberg | 210/635 |
| 4,415,665 | 11/1983 | Mosbach | 435/179 |

FOREIGN PATENT DOCUMENTS

| | | | |
|---|---|---|---|
| 144354 | 8/1983 | Japan | 435/215 |

OTHER PUBLICATIONS

Anal. Chem.—vol. 53—No. 3—Mar. 1981—pp. 489–495, "Liquid Chromatographic Separation of Amino Acids, Peptides and Derivatives on a Porous Polystyrene–Divinylbenzene Copolymer" by Z. Iskandarani and D. Pietrzyk.

*Primary Examiner*—P. E. Konopka

*Attorney, Agent, or Firm*—Henry C. Nields

[57] ABSTRACT

A biospecific adsorbent comprising pyroglutamyl-lysyl-leucyl-argininal combined with a water-insoluble support is provided. This biospecific adsorbent is useful as an adsorbent for use in affinity chromatography and can be utilized for the purification of proteases such as urokinase.

10 Claims, No Drawings

WATER-INSOLUBLE BIOSPECIFIC ABSORBENT CONTAINING ARGININAL DERIVATIVE

BACKGROUND OF THE INVENTION

Protease is a proteolytic enzyme and there are known various kinds of protease, including those showing an antiinflammatory and antihydropic effect, those showing a pus dissolving action and those showing a blood coagulation inhibiting action. These proteases are applied to the preparation of pharmaceuticals. With such kinds of proteases, especially those which are administered to man through intravenous injection exclusively, such as urokinase, safety must be guaranteed in their application, and thus it is an essential requirement to obtain high-purity proteases.

Various techniques and methods have been developed for the purification of the crude preparations of proteases. Recently, the affinity chromatographic techniques using an adsorbent prepared from a substance having a high affinity for the protein to be purified and combined with a water-insoluble support as a ligand are applied to the purification of proteases. For instance, the following methods have been proposed for the purification of urokinase:

(1) A basic amino acid such as lysine or arginine or a derivative thereof is used as the ligand (Japanese Patent Publication No. 44193/1976, and Japanese Patent Laid-Open Nos. 20596/1976, 95183/1976 and 35481 to 35483/1976).

(2) A urokinase inhibitor contained in placental tissues, etc., is used as the ligand (Japanese Patent Publication No. 20597/1976).

In the method (1), however, the substance used as the ligand has no satisfactory affinity for urokinase and it is hardly possible to specifically adsorb urokinase from a solution with a high salt concentration. The method (2) is rather impractical because, in this method, an inhibitory substance found only in a small quantity in the animal tissues is used as the ligand.

SUMMARY OF THE INVENTION

The present inventors have synthesized and studied various kinds of ligands in search for a method capable of producing high-purity protease and found as a result that a substance prepared by combining pyroglutamyl-lysyl-leucyl-argininal (hereinafter referred to as argininal derivative) with a water-insoluble support can adsorb protease and is also capable of eluting it easily by a mere pH adjustment.

This invention was achieved on the basis of this finding.

The adsorbent of this invention is prepared from said argininal derivative by combining the ε-amino group in the lysine moiety thereof with a water-insoluble support, and said argininal derivative used as the ligand can be synthesized in great volume from leupeptin (acetyl and propionyl-L-leucyl-L-leucyl-L-argininal), so that the adsorbent of this invention has the advantage that its production is easy.

Further, use of the adsorbent of this invention for the production of, for example, high-purity urokinase leads to the following advantages:

(1) A wider range of hydrogen ion concentration can be used for the adsorption of urokinase than usable in the conventional methods. For example, a pH range of 5 to 10, preferably 6 to 8, can be used.

(2) The influence of the salt concentration is less than in the conventional methods, and no specific desalting step is required prior to the adsorbing operation.

(3) Urokinase can be eluted and recovered in a high yield from said adsorbent by merely lowering its pH.

(4) Since the ligand used in this invention has a urokinase inhibiting action, urokinase remains inactive while it is in contact with the adsorbent, so that it stays substantially free of the actions causative of molecular weight reduction, such as self digestion, and hence it is possible to obtain a high-molecular weight urokinase having a high medicinal efficacy.

(5) Since the adsorbent can specifically adsorb urokinase, the purification efficiency is high and hence high-quality urokinase can be obtained.

DETAILED DESCRIPTION OF THE INVENTION

The water-insoluble support used in this invention is not subject to any specific definition except that it should have a functional group to which the ε-amino group in the lysine moeity of the argininal derivative is bondable and thus, for example, crosslinked polyacrylamide resins or macromolecular polysaccharide may be used. Typical examples of such crosslinked polyacrylamide resins are Bio-Gel P, Hydrazide Bio-Gel P and Bio-Gel CM (all being products of Bio-Rad Lab.). Exemplary of macromolecular polysaccharide are agarose gels such as Sepharose 2B, Sepharose 4B, Sepharose 6B, CH-Sepharose 4B (All being products of Pharmacia Inc.) and Bio-Gel A (a product of Bio-Rad), crosslinked dextran gels such as Sephadex and CM-Sephadex (products of Pharmacia), and celluloses such as Cellex and Cellex CM (products of Bio-Rad). Among them, agarose gels are preferred.

The functional group in said water-insoluble support may be, for example, hydroxyl group, carboxyl group or carboxyl group derivatives. Examples of the supports having a hydroxyl group are Sepharose 2B, Sepharose 4B, Sepharose 6B, Bio-Gel A, Sephadex and Cellex, and those having a carboxyl group are Bio-Gel CM, CH-Sepharose 4B, CM-Sephadex and Cellex CM, while those having a carboxyl group derivative are Bio-Gel P having a carbamoyl group and Hydrazide Bio-Gel P having a hydrazinocarbonyl group.

The adsorbent of this invention can be produced by reacting an argininal derivative having its aldehyde group protected with said water-insoluble support having its functional group activated, and then removing the aldehyde-protecting group.

Di(lower alkyl) acetals such as dibutyl acetal are preferred as the aldehyde-protecting group.

The following methods are available for activating the functional group in the water-insoluble support: (1) in case the functional group is a hydroxyl group, a cyanogen halide is reacted with the hydroxyl group, and (2) in case the functional group is a carboxyl group, a carboxyl-activating method utilized in the peptide chemistry, such as an active esterification method or an acid anhydride method is used. In this invention, however, a method using succinimide or a water-soluble carbodiimide is preferred.

The reaction between an argininal derivative having its aldehyde group protected and an activated water-insoluble support by, for instance, using a water-soluble carbodiimide can be accomplished by reacting them in a solvent with a pH of 3 to 7, preferably 4 to 6, at a temperature of 25° to 45° C., preferably 35° to 40° C., for a period of 10 to 30 hours, preferably 15 to 25 hours. As the water-soluble carbodiimide used in this reaction, 1-ethyl-3-(3-dimethylaminopropyl)carbodiimide, 1-cyclohexyl-3-(2-morpholinoethyl)carbodiimide and the like may be cited. The amount of the water-soluble carbodiimide used is 1 to 20 g, preferably about 5 to 10 g per 100 ml of the gelled water-insoluble support.

As the solvent, a salt solution or a buffer solution capable of maintaining the pH at 3 to 7, for example, a 0–50% dimethylformamide or dioxane solution may be used.

Commercially available supports include those in which the functional group has been activated by succinimide or an epoxy group, such as Activated CH-Sepharose 4B and Epoxy-activated Sepharose 4B, and there is no need of re-activation in using such supports and they may be immediately reacted with an argininal derivative having its aldehyde group protected.

To remove the aldehyde-protecting group from the reaction product, the latter is hydrolyzed in a buffer solution with a pH of 1 to 4, preferably 2 to 3, at a temperature of 20° to 50° C., preferably 30° to 45° C., for a period of 24 to 120 hours, preferably 48 to 96 hours. The buffer solution used in this hydrolysis may have a composition comprising a mineral acid such as hydrochloric acid or phosphoric acid, or an organic acid such as tartaric acid, citric acid, lactic acid, succinic acid, or acetic acid, and its sodium or potassium salt.

In the adsorbent of this invention obtained in the manner described above, an argininal derivative serving as a ligand is combined in an amount of 0.1 to 10 μmol per ml of the water-insoluble support, but it is desirable for the purification of protease that the support combined in an amount of 0.5 to 5 μml.

A method of obtaining a high-purity protease such as urokinase by using the adsorbent of this invention is, for example, as follows.

First, the adsorbent is packed in a column and its pH is adjusted to 5 to 10, preferably 6 to 8. Though it is not necessary to specifically regulate the ionic strength, it is desirable to have the column preequilibrated with a 0.025 to 0.5M buffer solution such as a sodium phosphate/phosphoric acid solution, a potassium phosphate/phosphoric acid solution, a sodium acetate/acetic acid solution or a tris(hydroxyamino)methane/hydrochloric acid solution.

Then a crude aqueous urokinase solution adjusted to a pH of 5 to 10, preferably 6 to 8, is passed through the above adsorbent column so that urokinase is adsorbed on said adsorbent. The adsorbent on which urokinase has been adsorbed is washed with the above-mentioned buffer solution and then urokinase is eluted with an acid solution, water-soluble salt solution or buffer solution with a pH of 1 to 4, preferably 2 to 3, whereby a high-purity urokinase solution can be obtained. The acid solution used for this elution may be an aqueous solution of citric acid, tartaric acid, lactic acid, succinic acid, acetic acid, phosphoric acid, hydrochloric acid or the like. The water-soluble salt solution may be, for example, a sodium chloride/hydrochloric acid solution, a potassium chloride/hydrochloric acid solution or a sodium sulfate/sulfuric acid solution. As the buffer solution, one may use a sodium phosphate/phosphoric acid solution, a potassium phosphate/phosphoric acid solution, a citric acid/sodium citrate solution, succinic acid/borax, lactic acid/sodium lactate, acetic acid/sodium acetate, tartaric acid/sodium tartarate and the like.

The above process can be carried out either on a column system or on a batchwise system.

The L-argininal derivative combined as a ligand in the preparation of the adsorbent of this invention can be produced, for example, in the following way.

First, a reactive derivative in the carboxyl group of an N-(un)protected L-pyroglutamic acid and an ε-N-protected L-lysine are reacted to obtain an N-(un)-protected L-pyroglutamyl-ε-N-protected L-lysine. Used as the N-protecting group in this reaction is a group which can be removed by a catalytic reduction, such as benzyloxycarbonyl group or p-methoxybenzyloxycarbonyl group. As the reactive derivative, there may be used active esters such as N-hydroxysuccinimide ester, p-nitrophenyl ester, or 2,4,5-trifluorophenyl ester.

As the solvent, a mixture consisting of a solvent such as dioxane, dimethylformamide, or dimethylacetamide and water may be used. Then the thus obtained N-(un)-protected L-pyroglutamyl-ε-N-protected L-lysine and an aldehyde-protected L-leucyl-L-argininal (see Japanese Patent Laid-Open No. 37185/1980, Example 1) obtained by hydrolyzing an aldehyde-protected L-leupeptin with thermolysin are condensed in a solvent. This condensation can be accomplished by methods generally used for forming the peptide linkage, for example, a method using a carbodiimide such as dicyclohexylcarbodiimide or ethyldimethylaminopropylcarbodiimide alone, or a method using such carbodiimide in combination with N-hydroxybenzotriazole, N-hydroxysuccinimide, N-hydroxy-5-norbornene-2,3-dicarboximide or the like, or a method using a condensing agent such as diphenylphosphoryl azide or 1-ethoxycarbonyl-2-ethoxy-1,2-dihydroquinone. As the aldehyde-protecting group used in this reaction, a dialkyl acetal such as di-n-butyl acetal may be cited. The solvent used for said condensation may be of the conventional type. The condensate is then catalytically reduced to remove the N-protecting group and then further hydrolyzed to remove the aldehyde-protecting group, thereby obtaining an L-argininal derivative. The catalytic reduction can be accomplished in the usual way by using palladium black or such in a solvent such as methanol. The hydrolysis can be performed by using approximately 0.3 to 0.5N mineral acid or an organic acid such as succinic acid or oxalic acid in a solvent miscible with water, such as methanol, ethanol, acetone, acetonitrile, dimethylformamide, tetrahydrofuran, or dioxane.

The present invention will now be described in further detail by way of the embodiments thereof.

EXAMPLE 1

(a) Synthesis of N-benzyloxycarbonyl-L-pyroglutamyl-ε-N-benzyloxycarbonyl-L-lysine 3.5 g of N-benzyloxycarbonyl-L-pyroglutamic acid N-hydroxysuccinimide ester and 2.5 g of ε-N-benzyloxycarbonyl-L-lysine were suspended in a mixed solution of 100 ml of N,N'-dimethylformamide and 100 ml of water under ice cooling and, after addition of 1.4 ml of triethylamine, the suspension was stirred at room temperature for 20 hours. 1,000 ml of water was added to the resulting reaction solution and its pH was adjusted to 2 with hydrochloric acid. The formed precipitate was filtered and recrystallized from methanol to obtain 2.6 g of colorless needle-like crystals.

M.p.: 206°-208° C.

$[\alpha]_{578}^{24.5}=9.7°$ (C=0.3, in DMF)

| Elemental analysis ($C_{27}H_{31}N_3O_8$): | C | H | N |
|---|---|---|---|
| Calculated: | 61.68 | 5.94 | 8.00 |
| Found: | 61.70 | 6.03 | 7.98 |

(b) Synthesis of N-benzyloxycarbonyl-L-pyroglutamyl-ε-N-benzyloxycarbonyl-L-lysyl-L-leucyl-L-argininal dibutyl acetal hydrochloride 1.9 g of N-benzyloxycarbonyl-L-pyroglutamyl-ε-N-benzyloxycarbonyl-L-lysine obtained in Example 1(a) and 1.9 g of L-leucyl-L-argininal dibutyl acetal hydrochloride obtained by the method shown in Japanese Patent Laid-Open No. 37185/1980 were suspended in a mixed solution of 50 ml of ethyl acetate and 50 ml of dioxane, and to the resulting suspension were added 570 mg of N-hydroxybenzotriazole and 590 μl of triethylamine, and then further 870 mg of dicyclohexylcarbodiimide under ice cooling. Then the solution was returned to room temperature and stirred for 20 hours. After distilling off the solvent under reduced pressure, the residue was subjected to column chromatography using silica gel as support and developed with a 4:2:1:1 (v/v) mixture of butanol/butyl acetate/acetic acid/water to obtain 950 mg of a fraction positive to the Sakaguchi's reagent and showing an Rf value of 0.6.

$[\alpha]_{578}^{23}=-29.0°$ (C=1.1, in AcOH)

M.p.: 77°-81° C. (decomposed)

(c) 900 mg of the powder obtained in Example 1(b) was dissolved in 25 ml of methanol and subjected to a 2-hour catalytic reduction by using palladium black. After the reaction, palladium black was removed and the solvent was distilled off to obtain 700 mg of L-pyroglutamyl-L-lysyl-L-leucyl-L-argininal dibutyl acetal hydrochloride. Rd: 0.05 (using the same solvent as in Example 1).

M.P.: 103°-105° C.

$[\alpha]_{578}^{23.5}=-29.5°$ (C=0.8, in AcOH)

(d) 700 mg of L-pyroglutamyl-L-lysyl-L-leucyl-L-argininal dibutyl acetal hydrochloride obtained in Example 1(c) was suspended in a mixed solution of 200 ml of 0.1M morpholinoethanesulfonic acid and 200 ml of dioxane. To this suspension, with its pH adjusted to 5, were added 60 ml of CH-Sepharose® 4B and then portionwise 5 g in total of 1-ethyl-3-(3-dimethylaminopropyl)carbodiimide for a period of one hour under stirring. The resulting solution was further stirred at 37° C. for 20 hours. The obtained resin was washed with water and hydrolyzed with a 0.2M sodium citrate buffer solution of pH 2.5 at 40° C. for 60 hours to prepare 60 ml of gel-like CH-Sepharose resin combined with pyroglutamyl-lysyl-leucyl-argininal.

The amino acid analysis of the obtained gel gave the following results.

| Amount of ligand (μmol/ml*) | Amino acid analysis with 6N hydrochloric acid at 105° C. for 20 hours — Amino acids (mol/mol) | | |
|---|---|---|---|
| | Glutamic acid | Lysine | Leucine |
| 2.25 | 1.0 | 0.92 | 1.0 |

*Number of μmoles of the argininal derivative combined per ml of the water-insoluble support.

The amino acid analysis was conducted as follows.

One ml of the gel was washed with water and acetone, and dried under reduced pressure. The dried gel was hydrolyzed with 6N HCl for 20 hours at 105° C. A known amount of alanine was added to the hydrolysis as a standard. The amounts of amino acids were corrected based on the yield of the internal standard. The content of leucine was taken as the ligand content of the pyroglutamyl-lysyl-leucyl-argininal-Sepharose.

EXAMPLE 2

270 mg of L-pyroglutamyl-L-lysyl-L-leucyl-L-argininal dibutyl acetal hydrochloride obtained in Example 1(c) was suspended in a mixed solution of 78 ml of 0.1M morpholinoethanesulfonic acid and 78 ml of dioxane. To this suspension, with its pH adjusted to 5.0, were added 30 ml of CM-Biogel® A (100-200 meshes) (a product of Bio-Rad Lab.) and then portionwise 3 g of 1-ethyl-3-(3-dimethylaminopropyl)carbodiimide for a period of one hour under stirring. The resulting solution was further stirred at 37° C. for 24 hours. After the completion of the reaction, the obtained resin was washed with water and hydrolyzed with a 0.2M sodium citrate buffer solution of pH 2.5 at 40° C. for 70 hours. There was obtained 30 ml of pyroglutamyl-lysyl-leucyl-argininal-CM-Biogel® A.

| Amount of ligand (μmol/ml) | Amino acid analysis with 6N hydrochloric acid at 105° C. for 20 hours — Amino acids (mol/mol) | | |
|---|---|---|---|
| | Glutamic acid | Lysine | Leucine |
| 2.25 | 1.13 | 1.05 | 1.00 |

REFERENTIAL EXAMPLE 1

10 ml of the adsorbent prepared in Example 1(d) was packed in a column and sufficiently buffered with a 0.1M sodium phosphate buffer of pH 7.5 containing 0.1M sodium chloride. Then a solution containing crude urokinase with 1,960,000 IU (specific activity: 9,575 IU/mg protein) adjusted to a pH of 7.5 was passed through the column to have urokinase adsorbed on said adsorbent. Then the column was washed with said buffer solution and the urokinase adsorbed in the column was eluted by using 0.2M citric acid to obtain purified urokinase with 1,880,000 IU (specific activity: 1,151,381 IU/mg protein). The recovery was 96% and the specific activity increased about 12 times. The content of the high molecular weight species in the purified urokinase was 95%, which was the same as that in the crude urokinase.

REFERENTIAL EXAMPLE 2

30 ml of the resin prepared in Example 1(d) was packed in a column and sufficiently buffered with a phosphate buffer solution of pH 7.5 containing 0.1M sodium chloride. Then a solution containing crude urokinase (7,495 IU/mg protein) with 15,500,000 IU, adjusted to pH 7.5, was passed through the column to have urokinase adsorbed on said adsorbent. The column was washed with said buffer solution and the urokinase adsorbed in the column was eluted by using 0.2M citric acid (pH 2.5) to obtain purified urokinase (97,763 IU/mg protein) with 14,700,000 IU. The recovery was 95% and the specific activity increased about 13 times. The content of the high-molecular weight urokinase was 96%, the same as that before the purification treatment.

REFERENTIAL EXAMPLE 3

10 ml of the adsorbent prepared in Example 1(d) was packed in a column and sufficiently buffered with an acetate buffer solution (pH 7.5) containing 0.1M sodium chloride. Then a solution containing crude urokinase (37,371 IU/mg protein) with 750,000 IU and a pH of 7.5 was passed through the column. Then the column was washed with said buffer solution and urokinase was eluted from said column by using a 0.2M phosphate buffer solution (pH 2.5) to obtain purified urokinase (115,805 IU/mg protein) having 710,000 IU. The recovery was 95% and the specific activity increased about 4 times. The content of the high molecular weight urokinase was 98%, the same as that before the purification.

REFERENTIAL EXAMPLE 4

10 ml of the adsorbent obtained in Example 2 was packed in a column and sufficiently buffered with a 0.1M sodium phosphate buffer solution of pH 7.5 containing 0.1M sodium chloride. Then a solution containing partially purified urokinase of 1,392,000 IU (specific activity: 50,450 IU/mg Folin-Lowry protein) adjusted to pH 7.5 was introduced into said column to have urokinase adsorbed on said adsorbent. Then the column was sufficiently washed with said buffer solution and the urokinase adsorbed in the column was eluted by using 0.2M citric acid. The obtained urokinase had a specific activity of 134,208 IU/mg protein and 1,267,000 IU (yield: 91%). The content of the high molecular species in the purified urokinase was 95.3%, no difference from that in the starting material.

What is claimed is:

1. A biospecific adsorbent comprising pyroglutamyl-lysyl-leucyl-argininal covalently bound with a water-insoluble support.

2. The adsorbent according to claim 1 wherein the amount of pyroglutamyl-lysyl-leucyl-argininal covalently bound is 0.1 to 10 μmol per ml of the water-insoluble support.

3. The adsorbent according to claim 1 wherein the amount of pyroglutamyl-lysyl-leucyl-argininal covalently bound is 0.5 to 5 μmol per ml of the water-insoluble support.

4. The adsorbent according to any of claims 1 to 3 wherein the water-insoluble support is a polyacrylamide resin or macromolecular polysaccharide.

5. The adsorbent according to claim 4 wherein the macromolecular polysaccharide is agarose, dextran or cellulose.

6. CH-Sepharose covalently bound with pyroglutamyl-lysyl-leucyl-argininal.

7. CM-Biogel A covalently bound with pyroglutamyl-lysyl-leucyl-argininal.

8. A process for producing a biospecific adsorbent comprising pyroglutamyl-lysyl-leucyl-argininal covalently bound with a water-insoluble support, which comprises reacting L-pyroglutamyl-L-lysyl-L-leucyl-L-argininal having its aldehyde group protected with a water-insoluble support having its functional group activated, and then removing the aldehyde-protecting group.

9. The process according to claim 8 wherein the functional group is a hydroxyl group of a carboxyl group.

10. The process according to claim 8 or 9 wherein the activation of the functional group is effected with a cyanogen halide, succinimide or a water-soluble carbodiimide.

* * * * *